United States Patent [19]
Daugherty

[11] Patent Number: 5,423,291
[45] Date of Patent: Jun. 13, 1995

[54] GRAVITY FEED BUTTERFLY FEEDER WITH MESH PAD FEEDING STATIONS

[76] Inventor: Kenneth Daugherty, 151 Pine Hill Rd., Carlisle, Pa. 17013

[21] Appl. No.: 192,430

[22] Filed: Feb. 7, 1994

[51] Int. Cl.$^6$ .................... A01K 39/026; A01K 53/00
[52] U.S. Cl. .................... 119/77; 119/52.2; 449/48
[58] Field of Search .................. 119/72, 77, 57.8, 57.9, 119/51.5, 52.2, 52.3, 74, 73; 449/48, 9, 10, 11; 222/92, 585

[56] References Cited

U.S. PATENT DOCUMENTS

| | | | |
|---|---|---|---|
| 1,108,277 | 8/1914 | Thale | 449/10 |
| 2,267,883 | 12/1941 | Wood | 119/77 |
| 2,573,802 | 11/1951 | Mitchell | 119/77 |
| 2,600,103 | 6/1952 | Feck | 119/77 |
| 4,691,665 | 9/1987 | Hefner | 119/77 |
| 4,708,091 | 11/1987 | Schafer | 119/73 |
| 4,712,512 | 12/1987 | Schreib et al. | 119/52 R |
| 4,747,370 | 5/1988 | Olson | 119/52.2 |
| 4,958,595 | 9/1990 | Richman et al. | 119/52.2 |
| 5,002,913 | 3/1991 | Brown | 119/15 |
| 5,195,463 | 3/1993 | Lorenzana | 119/77 |
| 5,269,258 | 12/1993 | Brown | 119/57.9 |
| 5,303,674 | 4/1994 | Hyde, Jr. | 119/77 |

FOREIGN PATENT DOCUMENTS

| | | | |
|---|---|---|---|
| 2227819 | 1/1975 | France | 119/77 |
| 3149939 | 6/1983 | Germany | 119/52.2 |
| 48682 | 3/1921 | Sweden | 449/11 |

*Primary Examiner*—Todd E. Manahan
*Attorney, Agent, or Firm*—Leonard Bloom

[57] ABSTRACT

A feeder for butterflies has a reservoir to contain a feeding solution. The neck of the reservoir has a head and at least one feeding station is connected to the head. The feeding station is in fluid communication with the reservoir. A mesh-like pad is disposed in a well in the feeding station so that the butterfly may land on the pad.

12 Claims, 5 Drawing Sheets

GRAVITY FEED BUTTERFLY FEEDER WITH MESH PAD FEEDING STATIONS

The present apparatus relates to a feeder for butterflies to provide a feed solution, a container for the feed solution and a feed station in which the feed solution is available to the butterflies.

BACKGROUND OF THE INVENTION

The availability of bird feeders is well known as disclosed in U.S. Pat. Nos. 4,691,665 and 4,712,512. People enjoy the presence of beautiful birds and the feeders are a means of attracting the birds to gardens and to locations where the birds are easily viewed. Butterflies are also beautiful creatures which are of interest to people but only one feeder for butterflies known to the applicant. The Brown Company, Narragensett, Rhode Island markets a covered saucer-like container which holds food for butterflies but does not have the features of the present invention. The only other device related to butterflies of which the applicant is aware is a hibernation container as disclosed in U.S. Pat. No. 5,002,013. However, the beauty of the butterflies is not seen in this container. The bird feeder is not useful for butterflies because the butterfly must feed on a liquid nectar and cannot hover while feeding. The butterfly must land on a surface and draw up the liquid nectar with the butterfly's sucking mouthpart.

Thus, there exists a need for a feeder to make a liquid nectar continuously available to butterflies and to attract butterflies for the enjoyment of people.

SUMMARY OF THE INVENTION

A primary object of the invention is to provide a simple self-contained feeder to attract and feed butterflies.

Another object of the invention is to provide a device which can be suspended from a support and to contain and dispense a feed solution to a feeding station on which the butterfly may land.

In accordance with the teachings of the present invention, there is disclosed herein a feeder for butterflies including a reservoir having a closed upper end and an opposite end having a neck with an opening therein. A feed solution is contained in the reservoir. A head is removably connected to the neck of the reservoir. At least one feeding station is connected to the head and is in fluid communication With the reservoir. The head has an inner surface communicating with the opening in the neck of the reservoir. At least one channel extends through the head from the inner surface of the head to the at least one feeding station wherein the feed solution may flow from the reservoir to the feeding station. A well is formed in the at least one feeding station for storage of the feed solution. A mesh-like pad is disposed in the well in the at least one feeding station wherein butterflies may land on the pad and have access to the feed solution.

The neck of the reservoir may be threadably connected to the inner surface of the head. Alternately, the neck of the reservoir and the head may be connected by a snap-type connector.

A suspension means is provided to suspend the feeder from a support.

These and other objects of the present invention will become apparent from a reading of the following specification, taken in conjunction with the enclosed drawings.

DESCRIPTION OF THE PREFERRED EMBODIMENTS

Figure 1:
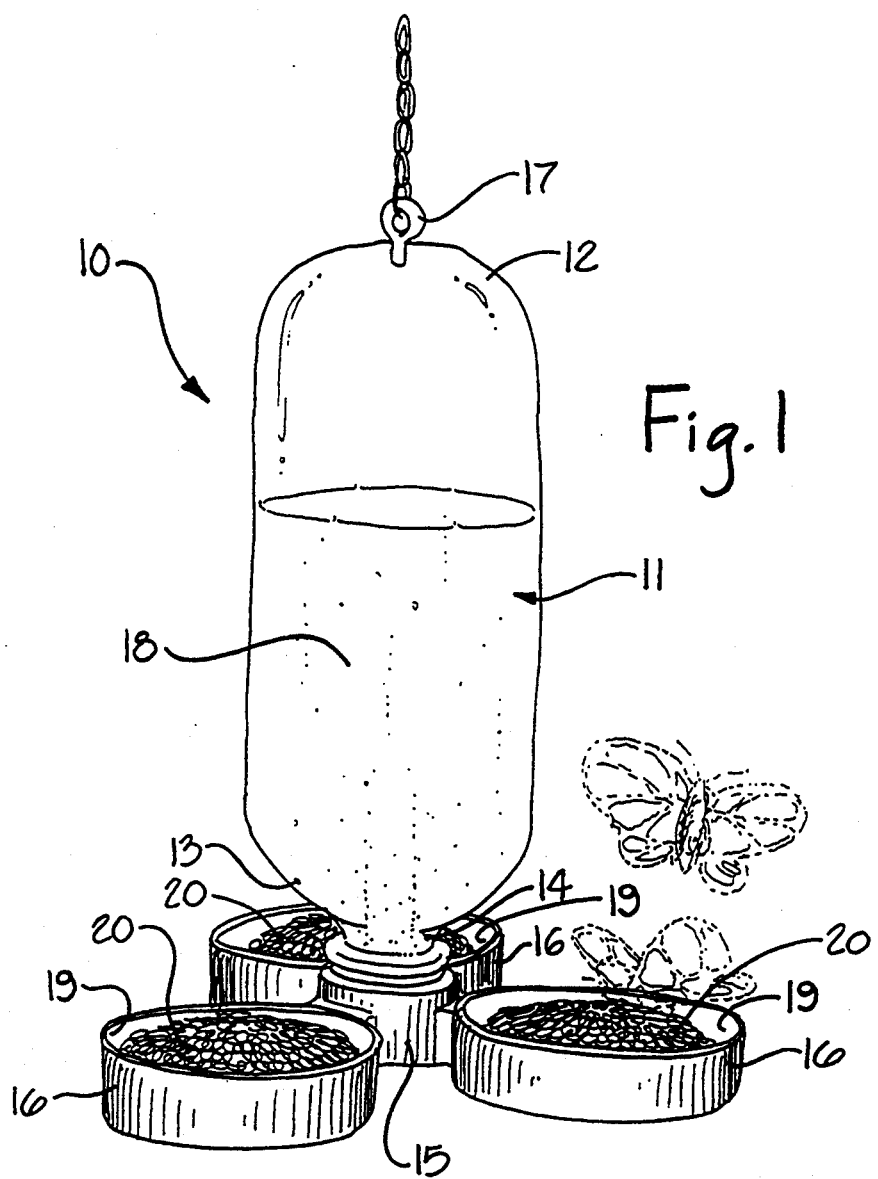
FIG. 1 is a perspective view of the butterfly feeder of the present invention.

Referring now to FIGS. 1–6, the butterfly feeder 10 has a reservoir 11 which has a closed upper end 12 and an opposite lower end, 13. The lower end 13 has a neck 14 with an opening in the neck 14. A head 15 is removably connected to the neck 14. At least one, and preferably more than one, feeding station 16 is connected to the head. A suspension means 17 is formed on the upper end 12 of the reservoir 11 so that the butterfly feeder 10 may be suspended from a tree, a pole, a house or other support. A feed solution 18 such as sugar water or other liquid which may be used to feed and attract butterflies is placed in the reservoir 11. The reservoir 11 is in fluid communication with the feeding station(s) 16 so that the feed solution 18 may pass through the head 15 and into a well 19 in the feeding station(s) 16. A mesh-like pad 20 is disposed in the well 19 in the feeding station 16 and approximately fills the well (FIGS. 3 and 4) so that the butterfly may land on the pad 20 and have access to the feed solution 18 through the openings in the mesh-like pad 20. Preferably, the mesh-like pad 20 is a non-absorbent plastic mesh.

Figure 5:
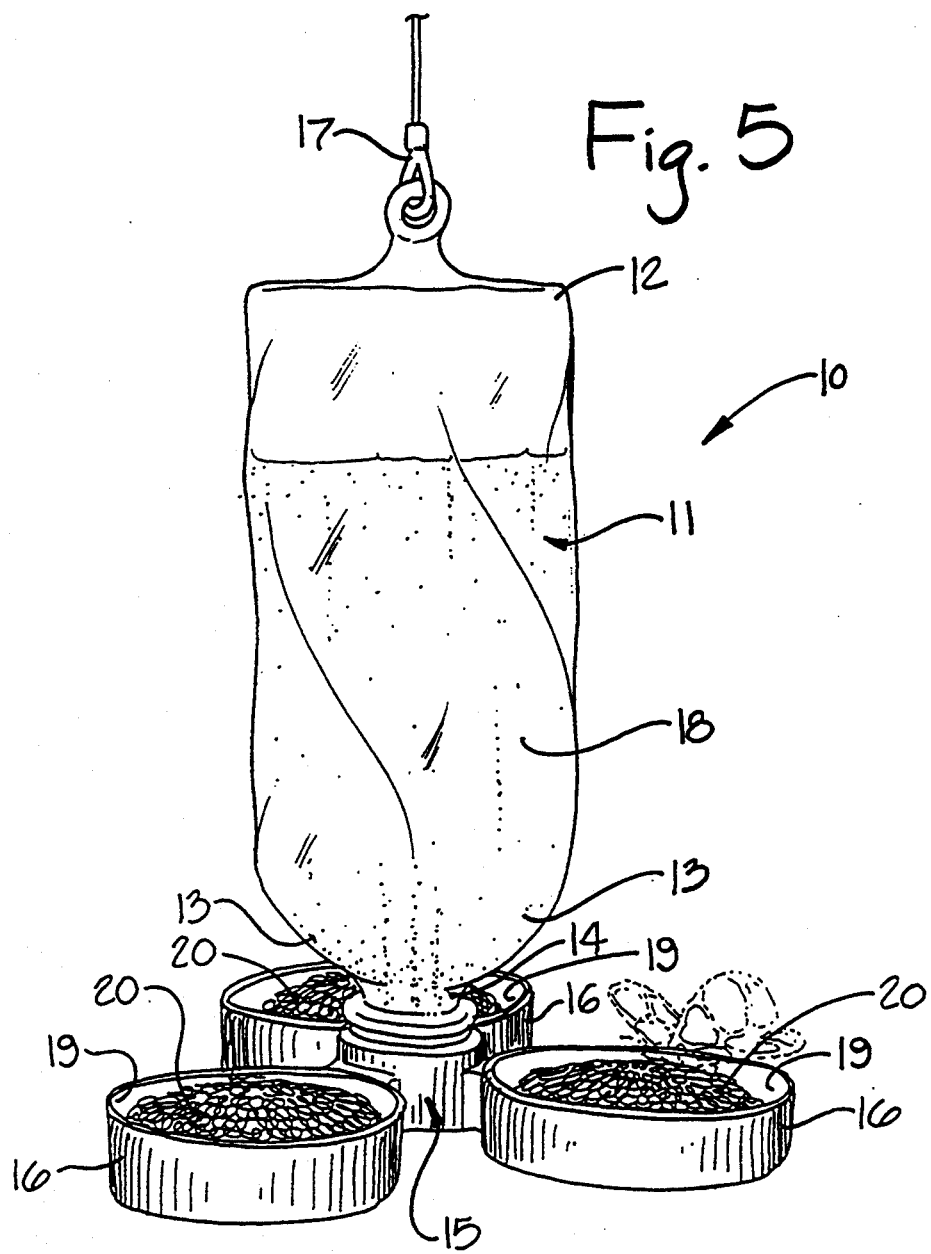
FIG. 5 is a perspective view of the present invention showing a collapsible reservoir.

The reservoir 11 may be a rigid container or may have flexible walls. Plastic bottles such as those which contain soft drink beverages have been used. Alternately the reservoir may have flexible walls which collapse inwardly as the feeding solution 18 empties from the reservoir to prevent any formation of vacuum or reduced pressure within the reservoir 11 (FIG. 5).

Figure 2:
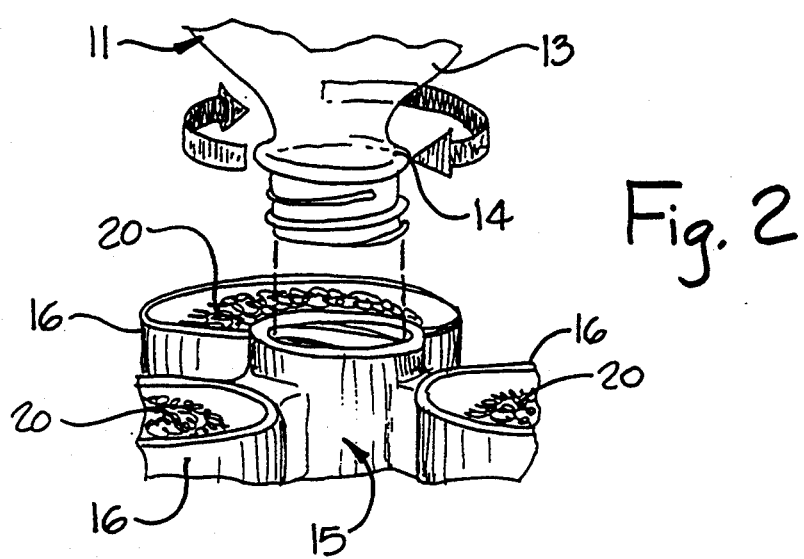
FIG. 2 is an enlarged perspective view of the threaded connection between the reservoir and the header.
Figure 3:
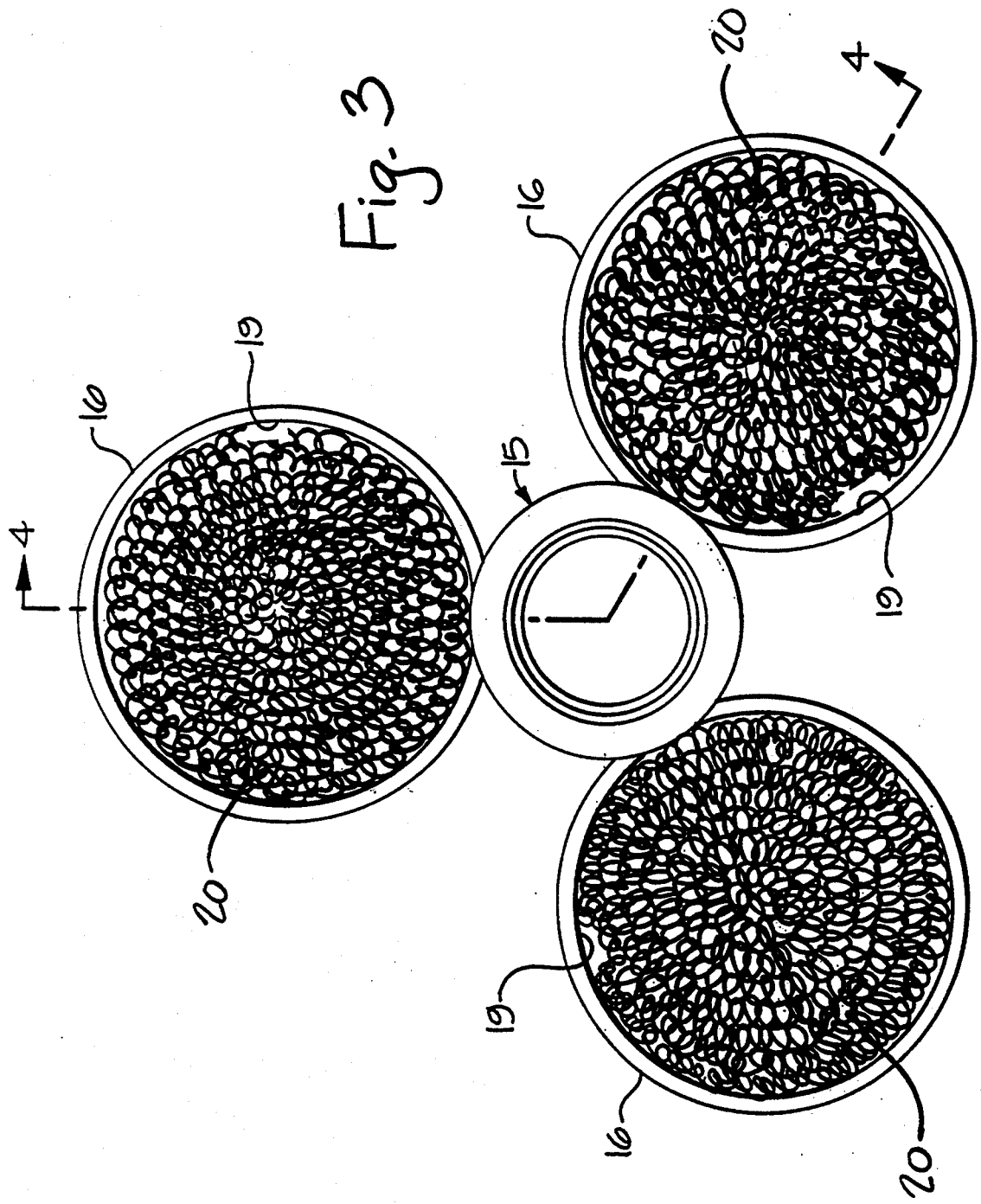
FIG. 3 is a top plan view of the header and the feeding stations.
Figure 6:
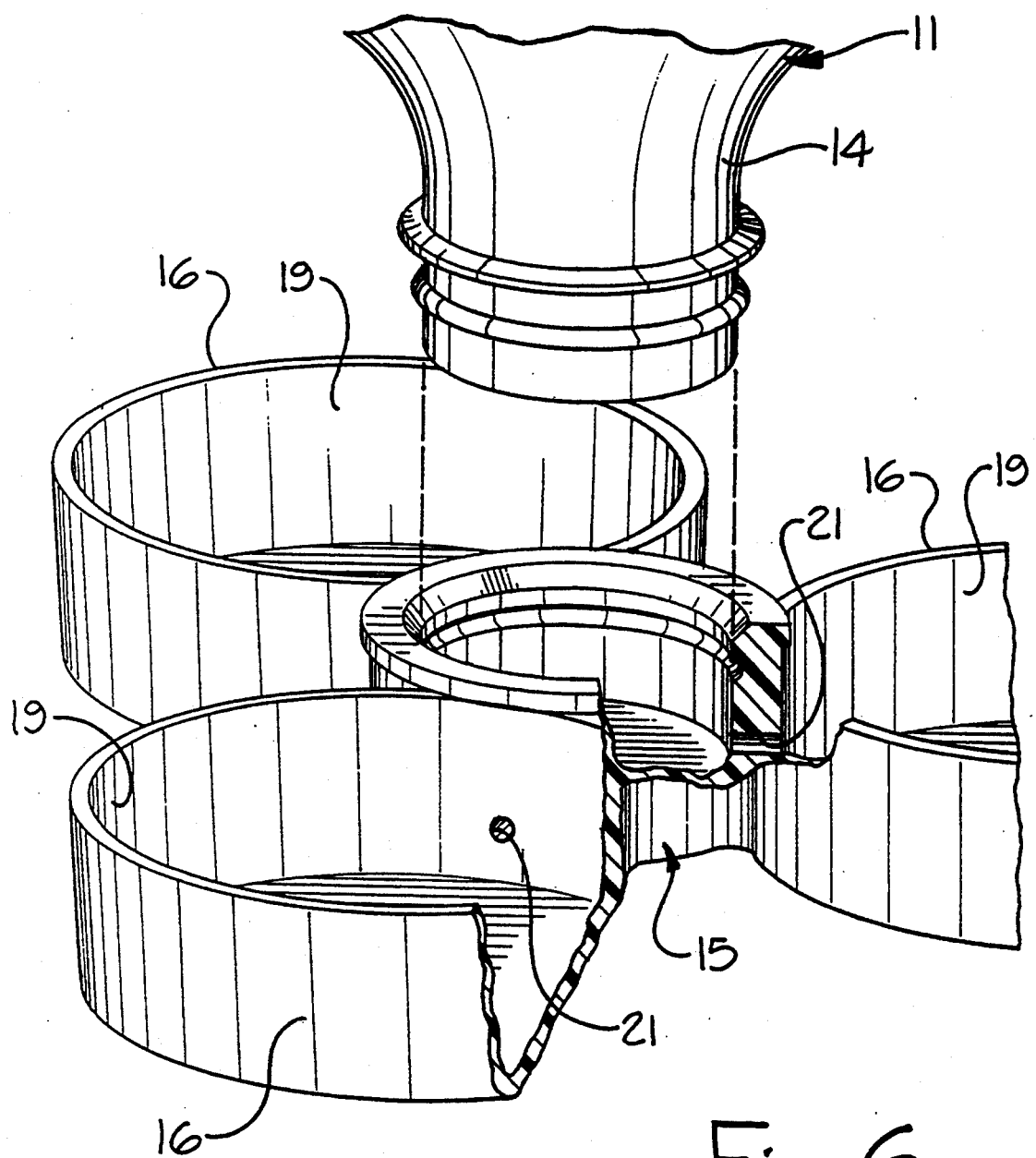
FIG. 6 is an enlarged perspective view of a snap fit connection between the reservoir and the header.

The neck 14 of the reservoir 11 may be threaded and the inner surface of the head 15 may be threaded to cooperate with the threaded neck 14 so that the head 15 is removably connected to the reservoir 11 (FIG. 2). A snap-type connection may alternately be used to connect the neck 14 of the reservoir 11 with the head 15 (FIG. 6).

Figure 4:
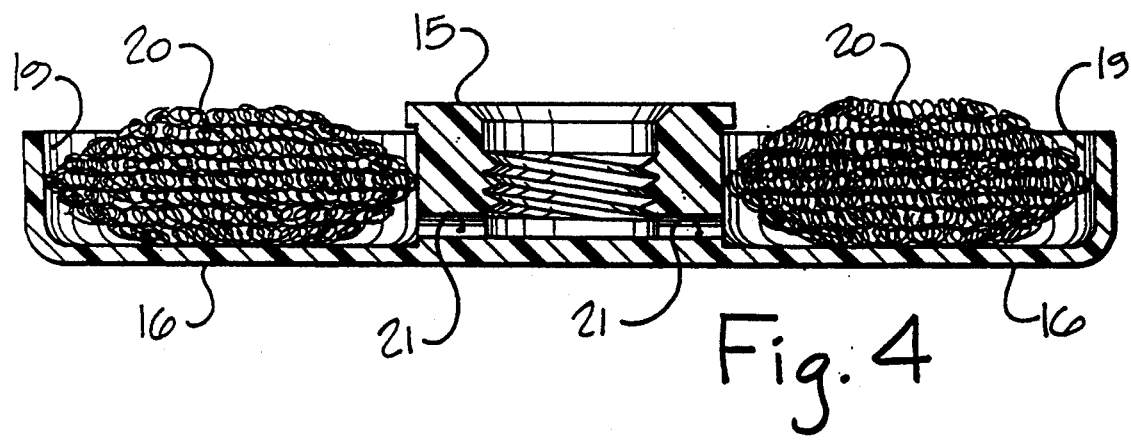
FIG. 4 is a cross-sectional view taken across the lines 4—4 of FIG. 3.

The head 15 is provided with at least one bore 21 therethrough to connect the inner surface of the head 15 with the feeding station 16. Preferably, two bores 21 connect the inner surface of the head 15 with each feeding station 16 so that the feed solution 18 may easily flow from the reservoir 11 into each feeding station 16 (FIG. 4).

Figure 7:
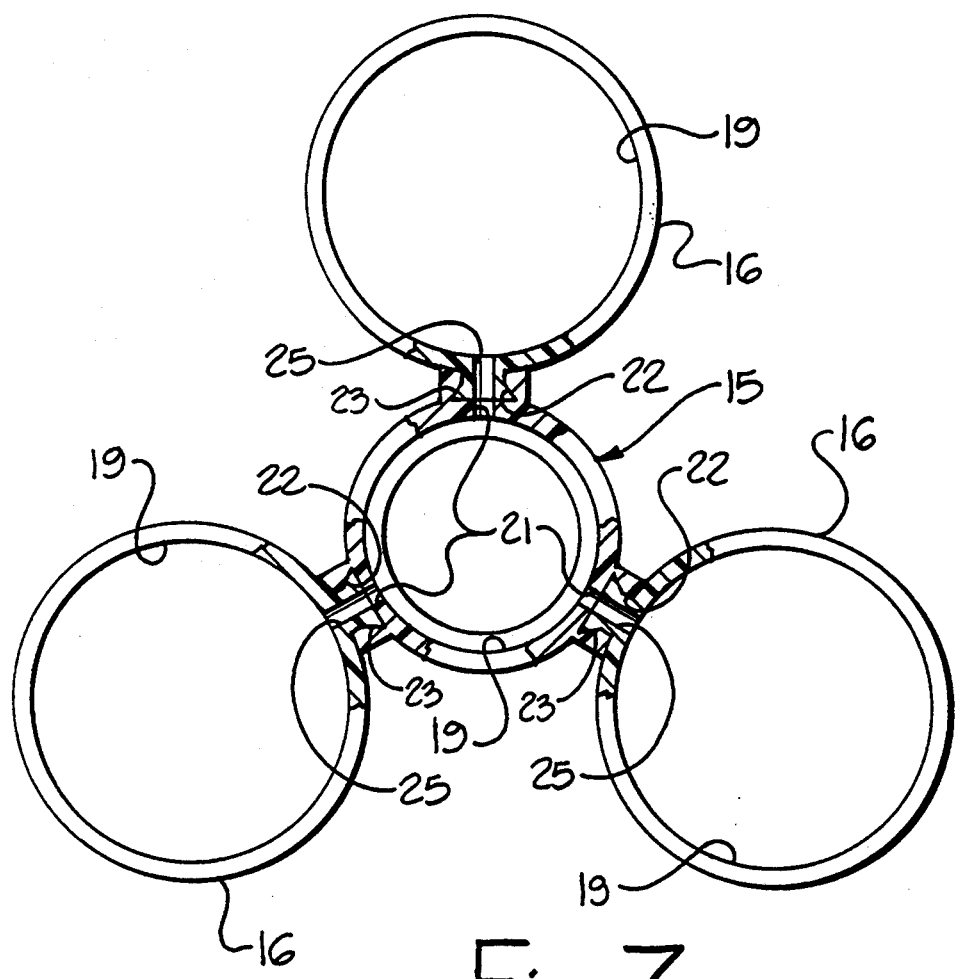
FIG. 7 is a top plan view showing the channels in the head and the stem on the feeding station for removable connection therebetween.

The outer surface of the head 15 may have at least one vertical channel 22 formed thereon and the feeding station 16 may have a stem 23 formed thereon such that the stem 23 may be received in the vertical channel 22 to removably connect the feeding station 16 to the head 15. The bores 21 in the head 15 pass through the vertical channel 22 and the stem 23 so that feed solution 18 may flow from the reservoir 11 into the feeding station 16. A plurality of spaced-apart vertical channels 22 may be formed around the circumference of the head 15 to accommodate a corresponding plurality of feeding stations 16 (FIG. 7).

Figure 8:
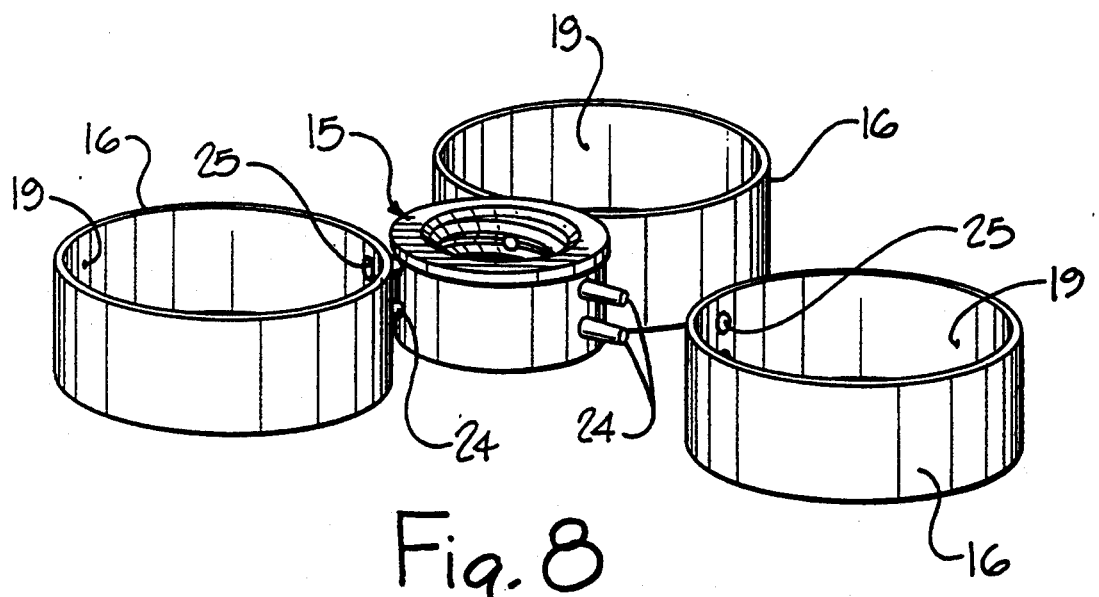
FIG. 8 is a perspective view showing tubes on the head and openings in the feeding station for connection of the feeding station to the head.

Alternately, the head 15 may have at least one and preferably two tapered tubes 24 extending outwardly from the outer surface of the head 15 at each position where a feeding station 16 is attached to the head 15. The bore 21 is formed in each tapered tube 24. Each feeding station 16 has corresponding openings 25 formed therein so that the feeding station 16 may be connected to the head 15 and the feed solution 18 may flow into the feeding station 16 (FIG. 8). If desired, the openings may be formed in the head 15 and the stems may be formed on the feeding station 16.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A feeder for butterflies comprising a reservoir having a closed upper end and an opposite end having a neck with an opening therein, a feed solution contained in the reservoir, a head removably connected to the neck of the reservoir, at least one feeding station connected to the head and in fluid communication with the reservoir;
    an open well formed in the at least one feeding station for storage of the feed solution;
    a mesh-like pad disposed within the well, and approximately filling the well in the at least one feeding station wherein butterflies may land on the mesh-like pad and have access to the feed solution through the mesh-like pad.

2. The feeder of claim 1, wherein the neck of the reservoir is threaded and the inner surface of the head is cooperatively threaded to removably connect the head to the reservoir.

3. The feeder of claim 1, wherein a snap-type connection is provided between the head and the neck of the reservoir.

4. The feeder of claim 1, further comprising a second channel extending from the inner surface of the head to the at least one feeding station.

5. The feeder of claim 1, further comprising suspension means connected to the upper end of the reservoir to suspend the feeder from a support.

6. The feeder of claim 1, wherein the mesh-like pad is a non-absorbent plastic mesh.

7. The feeder of claim 1, wherein the reservoir has flexible walls such that the walls collapse as the solution empties from the reservoir to prevent the formation of a vacuum in the reservoir.

8. The feeder of claim 1, further comprising three feeding stations disposed around, and connected to, the head.

9. The feeder of claim 1, wherein the at least one feeding station is removably connected to the head.

10. A feeder for butterflies comprising a reservoir having a closed upper end and an opposite end having a neck with an opening therein, a feed solution contained in the reservoir, a head removably connected to the neck of the reservoir, at least one feeding station connected to the head and in fluid communication with the reservoir;
    the head having an inner surface communicating with the opening in the neck of the reservoir, at least one channel extending through the head from the inner surface of the head to the at least one feeding station wherein the feed solution may flow from the reservoir to the feeding station;
    a well formed in the at least one feeding station for storage of the feed solution;
    a mesh-like pad disposed in the well in the at least one feeding station wherein butterflies may land on the pad and have access to the feed solution,
    wherein the at least one feeding station is removably connected to the head, and
    wherein the head has at least one vertical channel formed therein, the at least one feeding station having a stem formed thereon such that the stem may be received in the channel to connect said feeding station to the head.

11. A feeder for butterflies comprising a reservoir having a closed upper end and an opposite end having a neck with an opening therein, a feed solution contained in the reservoir, a head removably connected to the neck of the reservoir, at least one feeding station connected to the head and in fluid communication with the reservoir;
    the head having an inner surface communicating with the opening in the neck of the reservoir, at least one channel extending through the head from the inner surface of the head to the at least one feeding station wherein the feed solution may flow from the reservoir to the feeding station;
    a well formed in the at least one feeding station for storage of the feed solution;
    a mesh-likepad disposed in the well in the at least one feeding station wherein butterflies may land on the pad and have access to the feed solution,
    wherein the at least one feeding station is removably connected to the head, and
    wherein the head has at least one tapered tube extending outwardly therefrom, the at least one feeding station having at least one opening formed in a side thereof whereby said at least one tapered tube is cooperatively received in said at least one opening to connect said feeding station to the head, said at least one tapered tube further having a bore therethrough whereby the feed solution may flow to said feeding station.

12. A butterfly feeder, comprising a housing, a reservoir connected to the housing and containing a feeding solution, a plurality of circumferentially-spaced feeding stations carried by the housing radially thereof, each of the feeding stations having an open well formed therein, each of the wells having a mesh pad disposed therein, the mesh pad approximately filling the respective well and the housing having respective channel means formed therein for communicating the reservoir with the respective mesh pads in the wells on the feeding stations, such that the butterflies may land on the respective mesh pads and feed on the feeding solution through the respective mesh pad.

* * * * *